United States Patent
Wang et al.

(10) Patent No.: US 11,621,079 B2
(45) Date of Patent: Apr. 4, 2023

(54) CEREBRAL PERFUSION STATE CLASSIFICATION APPARATUS, METHOD AND DEVICE, AND MODEL TRAINING APPARATUS

(71) Applicant: BEIJING FRIENDSHIP HOSPITAL, CAPITAL MEDICAL UNIVERSITY, Beijing (CN)

(72) Inventors: Zhenchang Wang, Beijing (CN); Wei Zheng, Beijing (CN); Han Lv, Beijing (CN); Pengling Ren, Beijing (CN); Dehong Luo, Beijing (CN); Linkun Cai, Beijing (CN); Yawen Liu, Beijing (CN); Hongxia Yin, Beijing (CN); Pengfei Zhao, Beijing (CN); Jing Li, Beijing (CN); Dong Liu, Beijing (CN); Erwei Zhao, Beijing (CN); Tingting Zhang, Beijing (CN)

(73) Assignee: BEIJING FRIENDSHIP HOSPITAL, CAPITAL MEDICAL UNIVERSITY, Beijing (CN)

( * ) Notice: Subject to any disclaimer, the term of this patent is extended or adjusted under 35 U.S.C. 154(b) by 0 days.

(21) Appl. No.: 17/750,248

(22) Filed: May 20, 2022

(65) Prior Publication Data
US 2023/0056555 A1 Feb. 23, 2023

(30) Foreign Application Priority Data

Aug. 17, 2021 (CN) .......................... 202110943428.X

(51) Int. Cl.
*G16H 50/20* (2018.01)
*G06N 20/20* (2019.01)
(52) U.S. Cl.
CPC ............. *G16H 50/20* (2018.01); *G06N 20/20* (2019.01)

(58) Field of Classification Search
CPC .............................. G16H 50/20; G06N 20/20
See application file for complete search history.

(56) References Cited

U.S. PATENT DOCUMENTS

| 2016/0058303 | A1* | 3/2016 | Grady | A61B 5/7275 |
| | | | | 600/504 |
| 2018/0276820 | A1* | 9/2018 | Gibby | A61B 5/055 |
| 2020/0315455 | A1* | 10/2020 | Lee | A61B 5/7275 |

FOREIGN PATENT DOCUMENTS

| CN | 106919956 A | 7/2017 |
| CN | 111814284 A | 10/2020 |

OTHER PUBLICATIONS

Chinese Office Action from Corresponding CN Application No. 202110943428X, dated Dec. 7, 2021.

* cited by examiner

*Primary Examiner* — Gregory D. Moseley
(74) *Attorney, Agent, or Firm* — Maschoff Brennan

(57) ABSTRACT

The present disclosure discloses a cerebral perfusion state classification apparatus, method and device, and a model training apparatus. In the apparatus, a transceiver module is used for receiving physiological feature data from different data collection devices; and a processor is used for extracting physiological features from the physiological feature data; inputting the physiological features into a random forest model to cause a plurality of decision-making trees in the random forest model to predict a cerebral perfusion state type corresponding to the physiological features; and classifying a cerebral perfusion state based on the cerebral perfusion state type corresponding to the physiological features.

8 Claims, 3 Drawing Sheets

US 11,621,079 B2

CEREBRAL PERFUSION STATE CLASSIFICATION APPARATUS, METHOD AND DEVICE, AND MODEL TRAINING APPARATUS

FIELD

The present disclosure belongs to the technical field of computers, in particular to a cerebral perfusion state classification apparatus, method and device, and a model training apparatus.

BACKGROUND

A cerebral perfusion imaging technology is mainly used for reflecting a cerebral perfusion state of cerebral tissues. In the related technology, large-scale equipment such as computed tomography (CT) and magnetic resonance imaging (MM) are mostly used for examination, and then cerebral perfusion and cerebral functional states are assessed according to examination results.

However, the inspection equipment in the related technology is complicated in operation, and is often large in size, which makes it difficult to adapt to some special scenarios, such as aerospace scenarios and outdoor emergency scenarios. Therefore, a new solution needs to be proposed.

SUMMARY

In view of this, the present disclosure provides a cerebral perfusion state classification apparatus, method and device and a model training apparatus, which solve or partially solve the above technical problems.

In a first aspect, an embodiment of the present disclosure provides a cerebral perfusion state classification apparatus, the apparatus including:

a transceiver module used for receiving physiological feature data from different data collection devices, wherein the physiological feature data includes at least one of physiological index data, cervical blood flow data, and cerebral perfusion data;

a processor used for extracting physiological features from the physiological feature data; inputting the physiological features into a random forest model to cause a plurality of decision-making trees in the random forest model to predict a cerebral perfusion state type corresponding to the physiological features; and classifying a cerebral perfusion state based on the cerebral perfusion state type corresponding to the physiological features.

In a second aspect, an embodiment of the present disclosure provides a cerebral perfusion state classification method, the method including:

receiving physiological feature data from different data collection devices, wherein the physiological feature data includes at least one of physiological index data, cervical blood flow data, and cerebral perfusion data;

extracting physiological features from the physiological feature data;

inputting the physiological features into a random forest model to cause a plurality of decision-making trees in the random forest model to predict a cerebral perfusion state type corresponding to the physiological features; and classifying a cerebral perfusion state based on the cerebral perfusion state type corresponding to the physiological features.

In a third aspect, an embodiment of the present disclosure provides a cerebral perfusion state classification model training apparatus, the apparatus including:

a transceiver module used for receiving physiological feature data samples from different data collection devices, wherein the physiological feature data samples comprise at least one of a physiological index data sample, a cervical blood flow data sample, and a cerebral perfusion data sample;

a processor used for extracting physiological feature samples from the physiological feature data samples; inputting the physiological feature samples into a random forest model to cause a plurality of decision-making trees in the random forest model to predict a cerebral perfusion state type corresponding to the physiological feature samples;

the processor is further used for adjusting, based on a cerebral perfusion state type predicted by the random forest model and a pre-labeled mapping relation between the physiological feature data samples and cerebral perfusion state type samples, the random forest model, so as to cause a cerebral perfusion state type output by the adjusted random forest model to be consistent with the cerebral perfusion state type sample.

In a fourth aspect, an embodiment of the present disclosure provides a cerebral perfusion state classification model training method, including:

receiving physiological feature data samples from different data collection devices, wherein the physiological feature data samples include at least one of a physiological index data sample, a cervical blood flow data sample, and a cerebral perfusion data sample;

extracting physiological feature samples from the physiological feature data samples;

inputting the physiological feature samples into a random forest model to cause a plurality of decision-making trees in the random forest model to predict a cerebral perfusion state type corresponding to the physiological feature samples;

adjusting, based on a cerebral perfusion state type predicted by the random forest model and a pre-labeled mapping relation between the physiological feature data samples and cerebral perfusion state type samples, the random forest model, so as to cause a cerebral perfusion state type output by the adjusted random forest model to be consistent with the cerebral perfusion state type sample.

In a fifth aspect, an embodiment of the present disclosure provides an electronic device, including a memory and a processor.

The memory is used for storing a program;

the processor is coupled to the memory and used for executing the program stored in the memory to achieve:

receiving physiological feature data from different data collection devices, wherein the physiological feature data includes at least one of physiological index data, cervical blood flow data, and cerebral perfusion data;

extracting physiological features from the physiological feature data;

inputting the physiological features into a random forest model to cause a plurality of decision-making trees in the random forest model to predict a cerebral perfusion state type corresponding to the physiological features; and classifying a cerebral perfusion state based on the cerebral perfusion state type corresponding to the physiological features.

In a sixth aspect, an embodiment of the present disclosure provides a computer storage medium used for storing a computer program, the computer program, when executed, causes a computer to implement the following method:

receiving physiological feature data from different data collection devices, wherein the physiological feature data includes at least one of physiological index data, cervical blood flow data, and cerebral perfusion data;

extracting physiological features from the physiological feature data;

inputting the physiological features into a random forest model to cause a plurality of decision-making trees in the random forest model to predict a cerebral perfusion state type corresponding to the physiological features; and classifying a cerebral perfusion state based on the cerebral perfusion state type corresponding to the physiological features.

According to the solutions provided by the embodiments of the present disclosure, the physiological feature data from different data collection devices is received, such as the physiological index data, the cervical blood flow data, and the cerebral perfusion data. Thus, the processor extracts the physiological features from the physiological feature data, inputs the physiological features into the random forest model to cause the plurality of decision-making trees in the random forest model to predict the cerebral perfusion state type corresponding to the physiological features, and classifies a cerebral perfusion state based on the cerebral perfusion state type corresponding to the physiological features.

In the technical solutions of the present disclosure, by inputting the various physiological features into the Random Forest (RF) model, the plurality of decision-making trees in the RF model can predict the cerebral perfusion state types corresponding to the various physiological features, so as to achieve classification of the cerebral perfusion states, so that the cerebral perfusion states can be classified without large-scale inspection equipment, which greatly lowers the difficulty of implementing the cerebral perfusion status classification and extends the application scenarios of the cerebral perfusion status classification (such as aerospace scenes and outdoor emergency scenes). In addition, the RF model can also integrate more physiological features to more accurately distinguish various cerebral perfusion states, improve the accuracy of cerebral perfusion and cerebral function evaluation results, and assist doctors in finishing brain examination.

BRIEF DESCRIPTION OF THE DRAWINGS

In order to describe the embodiments of the present invention or the technical solutions in the prior art more clearly, drawings required to be used in the embodiments or the illustration of the existing art will be briefly introduced below. Obviously, the drawings in the illustration below are some embodiments of the present invention. Those ordinarily skilled in the art also can acquire other drawings according to the provided drawings without creative work. In the drawings.

DETAILED DESCRIPTION OF EXAMPLE EMBODIMENTS

Figure 1:
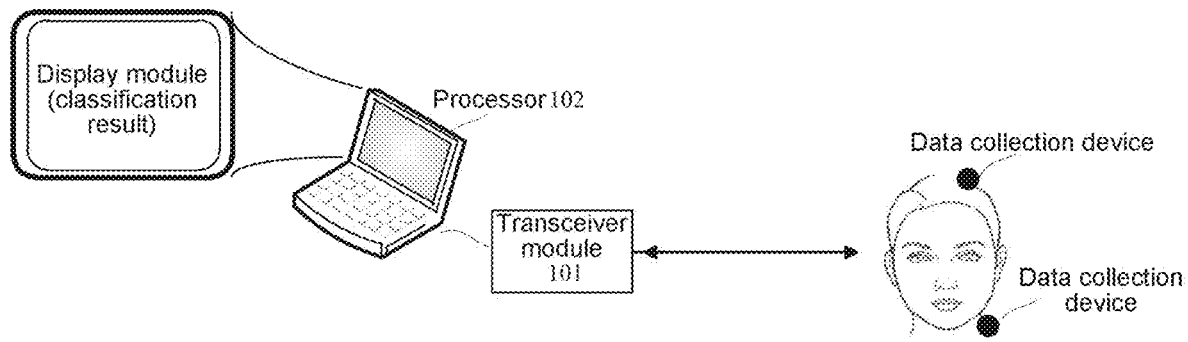
FIG. 1 is a schematic structural diagram of a cerebral perfusion state classification apparatus provided by an embodiment of the present disclosure.

Before introducing the technical solutions provided by the embodiments of the present disclosure, a brief introduction to the proper nouns involved in this document is given.

In order to make the objectives, technical solutions and advantages of the embodiments of the present disclosure clearer, the technical solutions in the embodiments of the present disclosure will be described clearly and completely below in combination with the drawings in the embodiments of the present disclosure. Apparently, the embodiments described are part of the embodiments of the present disclosure, not all the embodiments. Based on the embodiments in present invention, all other embodiments obtained by those of ordinary skill in the art without creative work shall fall within the protection scope of the present invention.

The terms used in the embodiments of the present disclosure are only for the purpose of describing the specific embodiments, and are not intended to limit the present disclosure. The singular forms of "a", "said", and "the" used in the embodiments of the present disclosure and the claims are also intended to include plural forms, unless the context clearly indicates other meanings. "Plurality" generally includes at least two, but does not exclude cases that include at least one.

It should be understood that the term "and/or" herein is only an association relationship that describes associated objects, and represents that there can be three relationships. For example, A and/or B can represent that: A exists alone, A and B exist simultaneously, and B exists alone. In addition, the character "I" herein generally indicates that the front and back associated objects are in an "or" relationship.

It should be further noted that the terms "comprise", "include", or any other variation thereof are intended to cover a non-exclusive inclusion, so that an article or system that includes a list of elements includes those elements and further includes other elements not expressly listed or further includes elements inherent to such an article or system. Without more constraints, an element preceded by "includes a . . . " does not preclude the existence of additional identical elements in the article or system that includes the element.

Firstly, it should be noted that the implementation background of the present disclosure is introduced. At present, a cerebral perfusion imaging technology is mainly used for reflecting a cerebral perfusion state of cerebral tissues. Through the cerebral perfusion imaging technology, an actual condition of a cerebral blood vessel can be restored as much as possible, and the cerebral perfusion and cerebral functional states can be assessed.

In the related technology, large-scale equipment such as CT and MRI are mostly used for examination, and then cerebral perfusion and cerebral functional states are assessed according to examination results.

However, inspection equipment in the related technology is complicated in operation, needs to be controlled by specialized technicians, is often large in size, and is usually installed in fixed places such as hospitals. Therefore, it is difficult to apply the cerebral perfusion imaging technology to some special scenarios. For example, in an aerospace scenario, due to the change of the gravity in a space environment (such as overweight and weightlessness) and a limited space in a space capsule, it is impossible to examine the astronaut's cerebral perfusion state through large-scale inspection equipment in the related technology, resulting in the inability to assess cerebral perfusion and cerebral functions in astronauts in the space environment. For another example, in an outdoor emergency scenario, accident sites are usually inaccessible (which are located in a remote location or with congestion nearby), and it is often difficult to transport the injured to a hospital with inspection equipment in time. Therefore, first-aid personnel often cannot know the cerebral perfusion state of the injured in time, affecting the treatment of the injured.

Therefore, there is a need to propose a technical solution that can solve at least one of the above problems.

An execution body of the technical solutions provided in the embodiments of the present disclosure may be one apparatus for a plurality of apparatuses. The apparatus may include, but is not limited to, an apparatus integrated on any terminal device such as a smart phone, tablet computer, a personal digital assistant (PDA), a smart TV, a laptop portable computer, a desktop computer, a smart wearable device, and a medical device. The apparatus includes a transceiver module used for receiving physiological feature data (such as physiological index data, cervical blood flow data, and cerebral perfusion data described below), and a processor used for processing the above physiological feature data. The processor of the apparatus may be mounted in the above-mentioned terminal device. The processor of the apparatus and a sensor may be integrated in the same device, or may be integrated in different devices respectively, which is not limited in the embodiment of the present disclosure. Optionally, the apparatus further includes a display module used for displaying a processing result of the apparatus, such as a screen in the terminal device.

In practical applications, the transceiver module of the apparatus can communicate with different data collection devices, so as to receive the physiological feature data acquired by these data collection devices through communication connection. Sensors with different functions are integrated in different data collection devices.

For example, an ultrasonic sensor is integrated in an ultrasonic data detection device, and the ultrasonic data detection device is provided on a target assessment object. The ultrasonic data detection device is implemented, for example, as a neck inspection device integrated with an ultrasonic sensor, the neck inspection device being connected to an apparatus integrated with a transceiver module. Of course, in order to adapt to various application scenarios, the connection between the neck examination apparatus and the apparatus integrated with a processor may be wired connection or wireless connection, such as WiFi, 5G, 4G, and Bluetooth.

In addition, the transceiver module can also communicate with a magnetic resonance data collection device, such as a superconducting magnetic resonance scanner.

In another embodiment, the transceiver module, the processor, and the data collection device may be integrated into the same system. For example, the transceiver module, the processor, and the data collection device may be integrated into a cerebral perfusion state monitoring system for a certain spaceflight scenario. Thus, a processing result is directly displayed in the cerebral perfusion state monitoring system, for example, voice information for expressing a cerebral perfusion state classification result is issued, or a cerebral perfusion state classification result is displayed. Alternatively, the cerebral perfusion state monitoring system sends the processing result to the terminal device, and the terminal device displays the processing result.

In fact, hardware structures of the apparatus may be set according to specific application scenarios. The embodiments of the present disclosure are only examples, and the specific settings are not limited.

It should be noted that no matter which hardware structure the execution body is implemented as, the core intent of the execution body is to:

extract a variety of physiological features from physiological feature data, so that cerebral perfusion state types corresponding to these physiological features are predicted through a plurality of decision-making trees in the random forest model, so as to achieve classification of cerebral perfusion states. In this way, the cerebral perfusion states can be classified without large-scale inspection equipment, which greatly lowers the difficulty of implementing the cerebral perfusion state classification and extends the application scenarios of the cerebral perfusion state classification (such as aerospace scenarios and outdoor emergency scenarios). In addition, the RF model can also integrate more physiological features to more accurately distinguish various cerebral perfusion states, improve the accuracy of cerebral perfusion and cerebral function evaluation results, and assist doctors in finishing brain examination.

The specific implementation modes of the technical solutions are introduced below in combination with specific embodiments.

As shown in FIG. 1, a schematic structural diagram of a cerebral perfusion state classification apparatus provided by an embodiment of the present disclosure is illustrated. It can be seen from FIG. 1 that the apparatus includes the following modules:

a transceiver module 101 used for receiving physiological feature data from different data collection devices;

a processor 102 used for extracting physiological features from the physiological feature data; inputting the physiological features into a random forest model to cause a plurality of decision-making trees in the random forest model to predict a cerebral perfusion state type corresponding to the physiological features; and classifying a cerebral perfusion state based on the cerebral perfusion state type corresponding to the physiological features.

Further, the apparatus may further include a display module used for outputting a processing result of the processor 102, such as a sensitive cerebral area, cerebral magnetic resonance data of the sensitive cerebral area, and cerebral perfusion state classification.

It can be understood that the transceiver module 101 and the processor 102 may be located on the same device. Alternatively, the transceiver module 101 is located locally while the processor 102 is located in a remote server. Of course, the two structures described here are only examples. In practical applications, a hardware structure for integrating the transceiver module 101 and the processor 102 may be selected according to specific application scenarios.

Firstly, the transceiver module 101 is used for receiving physiological feature data from different data collection devices. In an optional embodiment, the transceiver module 101 communicates with a data collection device, thereby receiving the physiological feature data from the data collection device through the communication connection with the data collection device.

Optionally, the physiological feature data includes, but is not limited to, at least one of physiological index data, cervical blood flow data, and cerebral perfusion data.

In the embodiment of the present disclosure, the physiological index data is mainly used to reflect physiological indexes of an assessment target. For example, the physiological index data includes, but is not limited to: the age, gender, heart rate, body temperature, blood pressure, and blood oxygen saturation of the assessment target. Optionally, these physiological index data can come from historical assessment data, such as pre-entered age and gender, or can be obtained by real-time detection, such as detecting the assessment target, so as to collect the heart rate, the body temperature, the blood pressure, and the blood oxygen saturation. For example, a sphygmomanometer is used to measure the blood pressure, and an intelligent mobile device is used to collect the heart rate, the body temperature, and the blood oxygen saturation. Of course, in another example, the above physiological index data can also be acquired by using the same physiological index data monitoring system, and the monitoring system is mounted on, for example, an ambulance or a space vehicle.

In the embodiment of the present disclosure, the cervical blood flow data is acquired by an ultrasonic data collection device. Since the blood flowing through the brain needs to be transported through the neck, the cervical blood flow data can reflect the cerebral perfusion to a certain extent, and provide a basis for prediction of a cerebral perfusion state.

In practical applications, the cervical blood flow data includes, but is not limited to, any one of the following data or a combination: cervical vascular blood flow data, vascular lumen shape change data, and vascular function data. Optionally, the cervical blood flow data is continuous periodic data, for example, a plurality of cervical blood flow data collected by the ultrasonic sensor based on a preset period. For example, the ultrasonic sensor continuously collects a plurality of groups of cervical blood flow data according to the preset period. Each group of cervical blood flow data includes a plurality of cervical blood flow signals, so that these signals constitute a corresponding cervical blood flow sequence.

In practical applications, the transceiver module 101 is connected to a data collection device integrated with an ultrasonic probe. For example, an ultrasonic sensor implemented based on an intravascular ultrasound (IVUS) technology is integrated into the data collection device. Alternatively, a Doppler ultrasonic probe can also be integrated.

In the embodiment of the present disclosure, the cerebral perfusion data includes, but is not limited to, cerebral magnetic resonance data. The brain magnetic resonance data includes, but is not limited to: Arterial Spin Labeling (ASL) data, Quantitative Susceptibility Imaging (QSM) data, quantitative Blood Oxygen Level Dependent (qBOLD) data.

The ASL data is obtained using an ASL technology, which is mainly used to reflect the cerebral perfusion (of a tested subject), such as an ASL sequence. ASL is a method for obtaining a cerebral perfusion image without using a contrast agent, which can reflect blood perfusion information of cerebral tissues from different angles. In the ASL technology, a saturation pulse or inversion sequence may be used to label endogenous protons in the blood at the upstream of a region of interest, and then signals are collected in the region of interest (such as an emphasized brain area). Thus, a non-invasive study on cerebral hemodynamics is realized.

Since ASL has natural repeatability, changes in blood perfusion can be observed repeatedly in a relatively short period of time. Therefore, optionally, the ASL technology is used to acquire a plurality of groups of ASL sequences as brain resonance samples, which are used for training a random forest model below, such as an ASL average time series sample.

The QSM data is mainly used to assess cerebral oxygen metabolism parameters, such as oxygen extraction fraction (OEF). The QSM data is a novel magnetic resonance imaging technology based on gradient echo, which can quantify the spatial distribution of the magnetic susceptibility in a biological tissue and become an important method to quantify the iron content in a living tissue.

The qBOLD data is mainly used to reflect the cerebral blood oxygen level (of the tested subject). Specifically, a qBOLD technology can effectively reflect functional changes such as cerebral perfusion and metabolic activities of the tested subject in various states (such as a resting state and a loaded state) by measuring changes in blood flow and blood oxygenation level. It is an effective means to study abnormal cerebral functional connections.

Specifically, a BOLD signal can be separated from venous oxygenation (Yv) and deoxygenated blood volume (DBV) to obtain qBOLD magnetic resonance images. In practical applications, the qBOLD magnetic resonance image can provide local and absolute in-vivo blood oxygen saturation measurements, so that the activity of nerve cells in various brain areas can be reflected according to changes of local signals, achieving the purpose of non-invasive study on the brain activity and providing a basis for the cerebral perfusion state classification below.

It is worth noting that the various physiological feature data introduced above can be used as sample data for training the random forest model below. For the collection process of the sample data, reference is made to the specific implementation mode in the related technology, which will not be described here.

The processor 102 in the embodiment of the present disclosure is a device used for analyzing and processing the various collected physiological feature data. The processor 102 may be a local processor 102, a remote server or server cluster, or a virtual processor 102 in a cloud server.

Based on receiving the physiological feature data through the transceiver module 101, the processor 102 needs to use the physiological feature data to predict a cerebral perfusion state type.

In fact, a cerebral perfusion state refers to a cerebral perfusion cerebral perfusion state. Based on different application requirements, cerebral perfusion states can be divided into various types. For example, the cerebral perfusion states are divided into normal cerebral perfusion, mildly high cerebral perfusion, moderately high cerebral perfusion, high cerebral perfusion, mildly low cerebral perfusion, moderately low cerebral perfusion, and low cerebral perfusion. For another example, the cerebral perfusion states can be divided into a normal/abnormal cerebral perfusion state in children, a normal/abnormal cerebral perfusion state in young people, and a normal/abnormal cerebral perfusion state in the elderly. Of course, the cerebral perfusion states can also be subdivided into more types according to a single evaluation dimension or multiple evaluation dimensions such as the gender and the physical condition (such as whether a person has underlying diseases).

In an optional embodiment, when extracting the physiological features from the physiological feature data, the processor 102 is specifically used for:

extracting a corresponding age, gender, blood pressure, heart rate, body temperature, and blood oxygen saturation based on the physiological index data; extracting a corresponding peak systolic velocity (PSV), end diastolic velocity (EDV), mean flow velocity, resistance index (RI), pulsatility index (PI), and systolic/diastolic ratio based on the cervical blood flow data; extracting corresponding cerebral perfusion kinetic parameters based on the ASL data and the QSM data; and taking the various physiological features extracted by the physiological index data, the cervical blood flow data, the ASL data and the QSM data as input features of the random forest model.

The physiological features extracted through the above steps are used as the input features of the random forest model for predicting the cerebral perfusion state. The specific description of the random forest model is as follows, which will not be described here.

Specifically, for any assessment target, the age, gender, blood pressure, heart rate, body temperature, and blood oxygen saturation of the assessment target are extracted from the physiological index data.

For any assessment target, a corresponding PSV, EDV, mean flow velocity, RI, PI, and systolic/diastolic ratio are calculated based on the cervical blood flow data. In practical applications, the above assessment parameters can be calculated by using an ultrasonic spectrogram, and a specific calculation method can refer to a calculation method commonly used in clinical practice. For example, the RI can be calculated by the following formula: RI=(PSV−EDV)/PSV, where PSV is the cervical peak systolic velocity, and EDV is the cervical end diastolic velocity.

For any assessment target, the cerebral perfusion kinetic parameters corresponding to the assessment target are calculated based on the ASL data, the QSM data, and the qBOLD data. The cerebral perfusion kinetic parameters include, but are not limited to: cerebral perfusion (CBF) and cerebral oxygen metabolism parameters. For example, the CBF is calculated using the ASL data. For example, the cerebral oxygen metabolism parameters such as the OEF can be calculated using the QSM data and the qBOLD data.

Further, after the above physiological features are extracted, optionally, the processor 102 uses the various physiological features extracted from the physiological index data, the cervical blood flow data, the ASL data and the QSM data as an input feature set of the random forest model.

Thus, based on the extracted physiological features, in an optional embodiment, when inputting the physiological features into the random forest model to cause a plurality of decision-making trees in the random forest model to predict a cerebral perfusion state type corresponding to the physiological features, the processor 102 is specifically used for:

inputting the physiological features into the random forest model; screening the physiological features to obtain a feature subset of the random forest model; respectively obtaining, based on the feature subset, a plurality of cerebral perfusion state types to be selected through the plurality of decision-making trees; making a vote based on the plurality of cerebral perfusion state types to be selected through the plurality of decision-making trees to obtain a plurality of voting results; and taking the cerebral perfusion state type to be selected with the most votes from among the plurality of voting results as a final output prediction result of the random forest model.

The random forest model is an algorithm model selected by introducing random features in a training process of the decision-making trees based on a bagging integrated algorithm composed of the decision-making trees. Various weak classifiers are integrated in the random forest model to form a new classifier model, so that the random forest model can achieve higher accuracy without feature selection.

Based on the input feature set introduced above, in the above steps, firstly, the processor 102 inputs the input feature set including the various physiological features into the random forest model. Optionally, the input feature set includes all the physiological features extracted from the physiological feature data.

Next, after the processor 102 inputs the physiological features into the random forest model, the following steps may also be used to implement feature selection in the random forest model, so as to further improve the prediction accuracy of the random forest model. When screening the physiological features to obtain a feature subset of the random forest model, the processor 102 is specifically used for:

acquiring feature importance of various physiological features to the random forest model under a preset cerebral perfusion state type; sorting the correlations between the various physiological features and the preset cerebral perfusion state type based on the feature importance; screening out, according to a sorting result, the physiological features that are the most correlated to the preset cerebral perfusion state type as the feature subset of the random forest model.

The various physiological characteristics include, but are not limited to: one or a combination of age, gender, blood pressure, heart rate, body temperature, blood oxygen saturation, PSV, EDV, average blood flow velocity, RI, PI, systolic/diastolic ratio, cerebral perfusion, and cerebral oxygen metabolism parameters.

Optionally, to facilitate model training, data labeling is usually performed. In an optional embodiment, it is assumed that the physiological characteristic data includes physiological characteristic data samples collected under different types of cerebral perfusion states. In this case, the processor 102 is further used for: labeling the cerebral perfusion state types corresponding to all the physiological characteristic data samples. The reference for labeling here is based on a cerebral perfusion state type detected when the physiological characteristic data is collected, such as the normal cerebral perfusion state, the high cerebral perfusion state, and the low cerebral perfusion state.

In the embodiment of the present disclosure, the feature importance is an index parameter used to measure the contribution of each input feature to a model prediction result. The prediction accuracy of the random forest model can be improved by feature importance measurement. Optionally, feature selection is performed by sorting the importance of all the input features in the random forest model to obtain a more efficient and reliable feature subset.

Specifically, by calculating the contribution of each input feature to each decision-making tree in the random forest, for each input feature, an average value of the contributions on the plurality of decision-making trees is used to represent the feature importance of the input feature. In practical applications, frequency statistics, a Gini index method, and an average accuracy reduction method can be used to calculate the feature importance of the input features.

It is worth noting that since logarithmic operation is not needed to be performed for a Gini index, the calculation is faster than other methods. Therefore, in the present disclosure, the Gini index method is further optionally used to calculate the feature importance of the input features. Specifically, by calculating the Gini index of the input feature sample under any cerebral perfusion state sample, the feature importance of the feature sample can be measured, so that the physiological features which are the most correlated to the preset cerebral perfusion state type are screened out from the various physiological features and used as the feature subset of the random forest model.

In an optional embodiment, when acquiring feature importance of various physiological features to the random forest model under a preset cerebral perfusion state type, the processor 102 is specifically used for:

for each of the physiological feature data sample collected in the preset cerebral perfusion state type, calculating a Gini index of the physiological feature in each physiological feature data sample for each decision-making tree in the random forest model, so as to obtain a Gini index of each physiological feature for the various decision-making trees in the random forest model.

Specifically, in this embodiment, an importance score of a physiological feature is denoted as VIM, and a Gini index value is denoted as GI. Assuming that there are m physiological features $X=X_1, X_2, \ldots X_n$, the score corresponding to the Gini index of each physiological feature $X_i$ is $VIM_i$, that is, an average change of the node split impurity of the $i^{th}$ feature in all decision-making tree of the random forest model. According to the calculation formula of the Gini index, in the $i^{th}$ decision-making tree, the Gini index of node k is: $GI_n = 1 - \Sigma_{k=1}^{|K|} p^2 mk$, where k represents that there are k types at feature node i, and $p_{mk}$ represents a ratio of type k in node m. The importance of the physiological characteristic $X_i$ at node m, that is, a variable of the Gini index before and after branching of node m, is: $VIM_{im}^{gini} = GI_m - GI_l - GI_r$, where $GI_l$ and $GI_r$ represent the Gini indexes of two new nodes after the branching, respectively. If the node where the physiological feature $X_i$ appear in decision-making tree j is in set M, the feature importance score of $X_i$ in the $j^{th}$ tree is: $VIM_{ji}^{gini} = \Sigma_{m \in M} VIM_{im}^{gini}$.

Further assuming that there are n trees in the random forest model:

$$VIM_i^{gini} = \sum_{j=1}^{n} VIM_{ji}^{gini}$$

the importance scores of the physiological features are normalized to obtain final importance scores of the physiological features:

$$VIM_j = \frac{VIM_i}{\sum_{j=1}^{c} j}.$$

Finally, the various physiological features are sorted in a descending order according to their importance scores, and the physiological features with lower importance scores (i.e., lower correlation) are deleted to obtain the feature subset of the random forest model.

Through the above steps, the feature selection can be performed on the various physiological features. Further, a more efficient and reliable feature subset can be obtained. Furthermore, the feature selection is performed for the physiological features collected under different cerebral perfusion states, so that more different types of physiological features can be further fused to further improve the prediction accuracy of various cerebral perfusion states, improve the accuracy of cerebral perfusion and cerebral functional assessment results, and assist doctors in finishing brain examination.

It is worth noting that in practical applications, the principle of other assessment methods for feature selection is similar, and will not be described here.

Further, based on the above selected feature subset, the processor 102 obtains, based on the feature subset, a plurality of cerebral perfusion state types to be selected through the plurality of decision-making trees; makes a vote based on the plurality of cerebral perfusion state types to be selected through the plurality of decision-making trees to obtain a plurality of voting results; takes the cerebral perfusion state type to be selected with the most votes from among the plurality of voting results as a final output prediction result of the random forest model.

Specifically, each decision-making tree makes a voting decision, and the state with the most votes is used as a final cerebral state. The calculation method for the final prediction result H(x) of the random forest model is:

$$H(x) = \text{argmax}_Y \sum_{i=1}^{k} I(h_i(x) = Y)$$

where $h_i(x)$ represents a classification prediction result of a single decision-making tree model, I( ) is a gender function, and Y is a target variable.

In practical applications, it is assumed that the extracted physiological features include: blood pressure, heart rate, body temperature, blood oxygen saturation, PSV, EDV, average blood flow velocity, RI, PI, systolic/diastolic ratio, cerebral perfusion, and cerebral oxygen metabolism parameters.

Based on this, the feature subset of the random forest model is firstly screened out, so as to output a cerebral perfusion state type to be selected that is determined by each decision-making tree based on the aforementioned feature subset through the multiple decision-making trees.

It is further assumed that the multiple decision-making trees include 5 decision-making trees. It is assumed that 3 of the 5 decision-making trees vote to decide that the cerebral perfusion state type is cerebral perfusion state type to be selected a, and the other 2 decision-making trees vote to decide that the cerebral perfusion state type is cerebral perfusion state type to be selected b. Based on this, cerebral perfusion state type to be selected a (that is, the cerebral perfusion state type to be selected with the most votes among the 5 voting results) is used as the final output prediction result of the random forest model.

Through the above steps, in practical applications, for the trained random forest model, based on the various input physiological features, the cerebral perfusion state types corresponding to these physiological features can be predicted, and the classification of cerebral perfusion states can be achieved.

Further, early warning information can also be displayed according to a classification result of the cerebral perfusion states, so as to prompt a user of the current cerebral perfusion state.

In practical applications, for example, it is assumed that the cerebral perfusion state type is Type I, which means that the cerebral perfusion is normal; it is assumed that the cerebral perfusion state type is Type II, which means that the cerebral perfusion is high; it is assumed that the cerebral perfusion state type is Type III, which means that the cerebral perfusion is low. Based on the above assumptions, if it is determined that the cerebral perfusion state type is Type I, "the current cerebral perfusion state is normal cerebral perfusion" will be displayed; if it is determined that the cerebral perfusion state type is Type II, "the current cerebral perfusion state is high cerebral perfusion" will be displayed; therefore, the doctors can be assisted in finishing the brain examination and assessment by means of the displayed content.

Of course, in addition to the first, second, and third types, the cerebral perfusion state types of all brain areas can also be set to three or more types, such as normal cerebral perfusion, mildly high cerebral perfusion, moderately high cerebral perfusion, high cerebral perfusion, mildly low cerebral perfusion, moderately low cerebral perfusion, and low cerebral perfusion. The level described here is actually determined according to a threshold range of the cerebral perfusion.

After a network mode and a using method thereof possibly used in the present disclosure have been introduced, an acquisition manner for training data used for training the above model is introduced below. For example:

Firstly, the cervical blood flow data of a target examination object can be collected through an ultrasonic sensor. Similar to the above description, the cervical blood flow data is converted into a cervical blood flow feature sequence, and the number of sequence elements is determined according to the number of the collected cervical blood flow data.

Next, cerebral MRI samples are introduced. The cerebral MRI samples mainly include a qBOLD sample, an ASL samples, and a QSM sample.

For example, functional magnetic resonance imaging (fMRI) is used to acquire cerebral magnetic resonance images as cerebral magnetic resonance samples. Optionally, preprocessing operations such as time slice correction, head movement correction, structural image and functional image registration, global normalization, spatial balance, and spatial normalization are performed on the cerebral magnetic resonance images to obtain a cerebral gray image which is used as the cerebral magnetic resonance sample. It is worth noting that fMRI is a neuroimaging way that uses magnetic resonance imaging to measure hemodynamic changes caused by neuronal activities.

Furthermore, the qBOLD sample, the ASL sample, and the QSM sample are extracted from the cerebral magnetic resonance samples.

In the present disclosure, the qBOLD sample is continuous periodic data collected by the qBOLD technology. Simply, a preset number of multiple qBOLD data samples can be collected during a measurement period. For example, 200 qBOLD data samples are collected during the measurement period. Therefore, the qBOLD data can reflect functional changes such as cerebral perfusion and metabolic activities in continuous time periods, which provide a basis for the screening of sensitive cerebral areas. The other two sample data collection methods are similar, and will not be introduced here. For specific collection methods, reference will be made to the related technology.

Optionally, corresponding classification labels can also be labeled for the cerebral magnetic resonance samples, so that the cerebral magnetic resonance samples carrying the classification labels are used in the training process of the cerebral perfusion state classification model described below.

In practical applications, the classification labels may be set with reference to a blood perfusion feature threshold. Specifically, the blood perfusion feature threshold is set to one or more numerical ranges. The numerical range includes a high perfusion threshold. Simply, each cerebral perfusion state type has a corresponding blood perfusion feature threshold range, and an end point of the range is, for example, the high perfusion threshold. If the blood perfusion feature value of a certain assessment target is greater than the high perfusion threshold of a certain type, the cerebral perfusion state of the assessment target does not belong to this type.

For example, a blood perfusion feature is, for example, a cerebral perfusion. Based on this, the blood perfusion feature threshold is a cerebral perfusion threshold.

In this embodiment, by inputting the various physiological features into the random forest model, the multiple decision-making trees in the random forest model predict the cerebral perfusion state types corresponding to the various physiological features, thereby achieving the cerebral perfusion state classification. Not only that, the cerebral perfusion states can be classified without large-scale inspection equipment, which greatly lowers the difficulty of implementing the cerebral perfusion state classification and extends the application scenarios of the cerebral perfusion state classification (such as aerospace scenarios and outdoor emergency scenarios). Furthermore, the random forest model can also integrate more physiological features to more accurately distinguish various cerebral perfusion states, improve the accuracy of cerebral perfusion and cerebral function evaluation results, and assist doctors in finishing brain examination.

Figure 2:
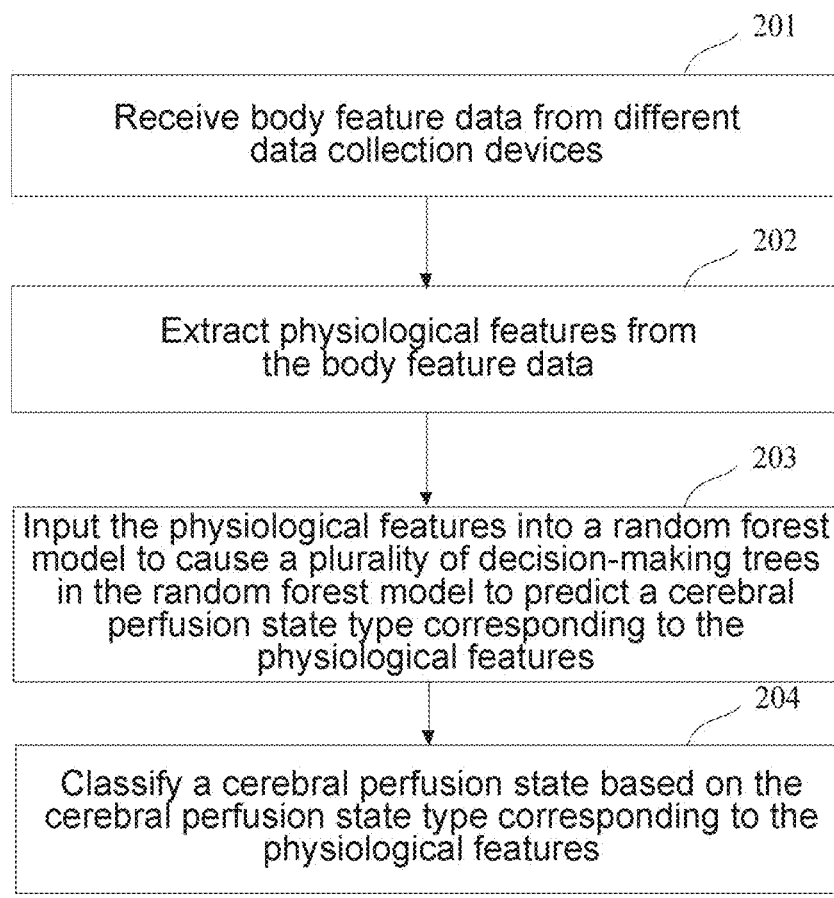
FIG. 2 is a flow chart of a cerebral perfusion state classification method provided by an embodiment of the present disclosure.

As shown in FIG. 2, a flow chart of a cerebral perfusion state classification method provided by an embodiment of the present disclosure is illustrated. The following specific steps are specifically included:

201, physiological feature data from different data collection devices are received;

202, physiological features are extracted from the physiological feature data;

203, the physiological features are input into a random forest model to cause a plurality of decision-making trees in the random forest model to predict a cerebral perfusion state type corresponding to the physiological features; and 204, a cerebral perfusion state is classified based on the cerebral perfusion state type corresponding to the physiological features.

Optionally, the cerebral perfusion data includes cerebral magnetic resonance data; the cerebral magnetic resonance data includes ASL data and QSM data.

The physiological feature data includes at least one of physiological index data, cervical blood flow data, and cerebral perfusion data.

The step that physiological features are extracted from the physiological feature data includes the following:

a corresponding age, gender, blood pressure, heart rate, body temperature, and blood oxygen saturation are extracted based on the physiological index data; a corresponding PSV, EDV, mean flow velocity, RI, PI, and systolic/diastolic ratio are extracted based on the cervical blood flow data; corresponding cerebral perfusion kinetic parameters are extracted based on the ASL data and the QSM data, wherein the cerebral perfusion kinetic parameters includes CBF and cerebral oxygen metabolism parameters; and the various physiological features extracted by the physiological index data, the cervical blood flow data, the ASL data and the QSM data are taken as input features of the random forest model.

Optionally, the step that the physiological features are input into a random forest model to cause a plurality of decision-making trees in the random forest model to predict a cerebral perfusion state type corresponding to the physiological features includes the following:

the physiological features are input into the random forest model; the physiological features are screened to obtain a feature subset of the random forest model; a plurality of cerebral perfusion state types to be selected are respectively obtained based on the feature subset through the plurality of decision-making trees; a vote is made based on the plurality of cerebral perfusion state types to be selected through the plurality of decision-making trees to obtain a plurality of voting results; the cerebral perfusion state type to be selected with the most votes from among the plurality of voting results is taken as a final output prediction result of the random forest model.

Optionally, the step that the physiological features are screened to obtain a feature subset of the random forest model includes the following:

feature importance of various physiological features to the random forest model under a preset cerebral perfusion state type are acquired; the correlations between the various physiological features and the preset cerebral perfusion state type are sorted based on the feature importance; the physiological features that are the most correlated to the preset cerebral perfusion state type are screened out, according to a sorting result, as the feature subset of the random forest model.

Optionally, the physiological feature data includes physiological feature data samples collected in different types of cerebral perfusion states.

The method further includes: cerebral perfusion state types corresponding to all the physiological feature data samples are labeled.

Optionally, a method for acquiring the feature importance includes at least one of the Gini index method, the frequency statistics method and the average accuracy reduction method.

Optionally, the step that feature importance of various physiological features to the random forest model under a preset cerebral perfusion state type is acquired includes the following:

for each physiological feature data sample collected in the preset cerebral perfusion state type, a Gini index of the physiological feature in each physiological feature data sample for each decision-making tree in the random forest model is calculated, so as to obtain a Gini index of each physiological feature for the various decision-making trees in the random forest model.

It is worth noting that the cerebral perfusion state classification method is similar to the implementation mode of the cerebral perfusion state classification apparatus provided in FIG. 1, and similar parts refer to the above, and will not be described here.

Figure 3:
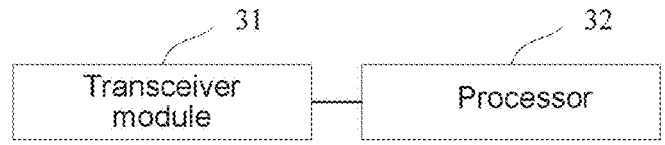
FIG. 3 is a schematic structural diagram of a cerebral perfusion state classification model training apparatus provided by an embodiment of the present disclosure.

FIG. 3 is a schematic structural diagram of a cerebral perfusion state classification model training apparatus provided by an embodiment of the present disclosure. As shown in FIG. 3, the apparatus includes a transceiver module 31 and a processor 32.

The transceiver module 31 is used for receiving physiological feature data samples from different data collection devices, wherein the physiological feature data samples comprise at least one of a physiological index data sample, a cervical blood flow data sample, and a cerebral perfusion data sample;

the processor 32 is used for extracting physiological feature samples from the physiological feature data samples; inputting the physiological feature samples into a random forest model to cause a plurality of decision-making trees in the random forest model to predict a cerebral perfusion state type corresponding to the physiological feature samples;

the processor 32 is further used for adjusting, based on a cerebral perfusion state type predicted by the random forest model and a pre-labeled mapping relation between the physiological feature data samples and cerebral perfusion state type samples, the random forest model, so as to cause a cerebral perfusion state type output by the adjusted random forest model to be consistent with the cerebral perfusion state type sample.

It is worth noting that the implementation principle of a cerebral perfusion state model trained by the above apparatus is similar to the implementation principle of the cerebral perfusion state classification apparatus provided in FIG. 1, and similar parts refer to the above, and will not be described here.

Figure 4:
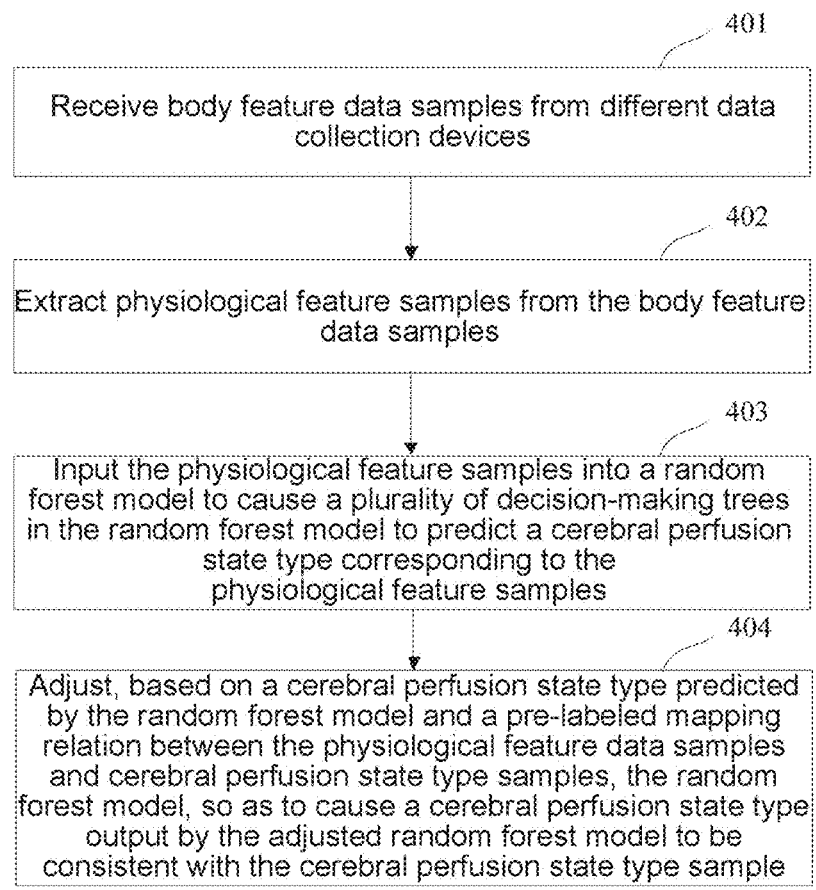
FIG. 4 is a flow chart of a cerebral perfusion state classification model training method provided by an embodiment of the present disclosure.

FIG. 4 is a flow chart of a cerebral perfusion state classification model training method provided by an embodiment of the present disclosure. As shown in FIG. 4, the method includes the following:

401, physiological feature data samples from different data collection devices is received, wherein the physiological feature data samples include at least one of a physiological index data sample, a cervical blood flow data sample, and a cerebral perfusion data sample;

402, physiological feature samples are extracted from the physiological feature data samples;

403, the physiological feature samples are input into a random forest model to cause a plurality of decision-making trees in the random forest model to predict a cerebral perfusion state type corresponding to the physiological feature samples;

404, the random forest model is adjusted based on a cerebral perfusion state type predicted by the random forest model and a pre-labeled mapping relation between the physiological feature data samples and cerebral perfusion state type samples, so as to cause a cerebral perfusion state type output by the adjusted random forest model to be consistent with the cerebral perfusion state type sample.

It is worth noting that the implementation principle of a cerebral perfusion state model trained by the above method is similar to the implementation principle of the cerebral perfusion state classification apparatus provided in FIG. 1, and similar parts refer to the above, and will not be described here.

Figure 5:
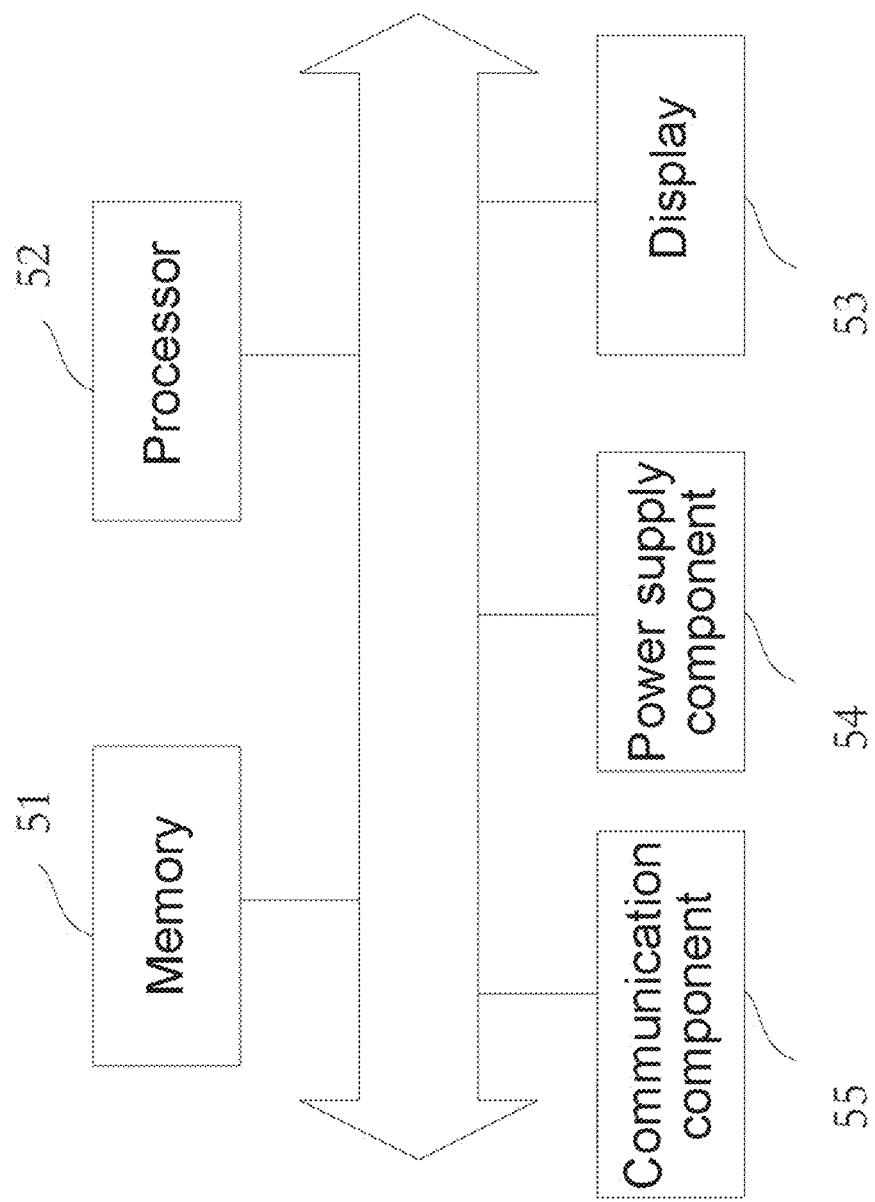
FIG. 5 is a schematic structural diagram of an electronic device provided by an embodiment of the present disclosure.

FIG. 5 is a schematic structural diagram of an electronic device provided by an embodiment of the present disclosure. As shown in FIG. 5, the electronic device includes a memory 51 and a processor 52.

The memory 51 is used for storing a program;

the processor 52 is coupled to the memory and used for executing the program stored in the memory to achieve:

receiving physiological feature data from different data collection devices, wherein the physiological feature data includes at least one of physiological index data, cervical blood flow data, and cerebral perfusion data;

extracting physiological features from the physiological feature data;

inputting the physiological features into a random forest model to cause a plurality of decision-making trees in the random forest model to predict a cerebral perfusion state type corresponding to the physiological features; and classifying a cerebral perfusion state based on the cerebral perfusion state type corresponding to the physiological features.

The above memory 51 may be configured to store various other data to support operations on a computing device. Examples of such data include instructions for any application or method operated on the computing device. The memory 51 may be implemented by any type of volatile or non-volatile storage devices or a combination thereof, such as Static Random Access Memory (SRAM), an Electrically Erasable Programmable Read-Only Memory (EEPROM), a Programming Read-Only Memory (EPROM), a Programmable Read-Only Memory (PROM), a Read-Only Memory (ROM), a magnetic memory, a flash memory, a magnetic disk or an optical disk.

When the above processor 52 executes the program in the memory 51, in addition to the above functions, other functions may also be implemented. Details may be referred to the descriptions of the foregoing embodiments.

Further, as shown in FIG. 5, the electronic device further includes: a display 53, a power supply component 54, a communication component 55 and other components. Only some components are schematically shown in FIG. 5, which does not mean that the electronic device only includes the components shown in FIG. 5.

Correspondingly, an embodiment of the present disclosure further provides a readable storage medium storing a computer program. The computer program, when executed by a computer, implements the steps or functions of the cerebral perfusion state classification methods provided by the above-mentioned embodiments.

The device embodiments described above are only illustrative, and the units described as separate components may or may not be physically separated, and the components displayed as units may or may not be physical units, that is, they may be located in one place, or may be distributed to multiple network units. Some or all of the modules may be selected according to actual needs to achieve the objectives of the solutions of the embodiments. Those of ordinary skill in the art can understand and implement the objectives without creative work.

Through the descriptions of the above implementation modes, those skilled in the art can clearly understand that all the implementation modes can be implemented by means of software and a necessary general hardware platform, and of course, can also be achieved by hardware. Based on this understanding, the above technical solutions essentially or the part that contributes to the existing technology can be embodied in the form of a software product, and the computer software product can be stored in a computer-readable storage medium, such as a read-only memory/random access memory (ROM/RAM), a magnetic disc, an optical disc, etc., and include several instructions to make a computer device (which may be a personal computer, a server, or a network device, etc.) execute the methods in all the embodiments or some parts of the embodiments.

It should be finally noted that: the above embodiments are only used to describe the technical solutions of the present invention, and not intended to limit the present invention. Although the present invention has been described in detail with reference to the foregoing embodiments, those ordinarily skilled in the art should understand that they can still modify the technical solutions described in all the foregoing embodiments, or equivalently replace some of the technical features, and these modifications or replacements do not depart the essences of the corresponding technical solutions from the spirit and scope of the technical solutions of all the embodiments of the present invention.

What is claimed is:

1. A cerebral perfusion state classification apparatus, comprising:
   a transceiver module used for receiving physiological feature data from different data collection devices, wherein the physiological feature data comprises at least one of physiological index data, cervical blood flow data, and cerebral perfusion data; wherein the cerebral perfusion data comprises cerebral magnetic resonance data, and the cerebral magnetic resonance data comprises arterial spin labeling (ASL) data, quantitative susceptibility mapping (QSM) data, and quantitative Blood Oxygen Level Dependent (qBOLD) data;
   a processor used for extracting physiological features from the physiological feature data; inputting the physiological features into a random forest model to cause a plurality of decision-making trees in the random forest model to predict a cerebral perfusion state type corresponding to the physiological features; and
   classifying a cerebral perfusion state based on the cerebral perfusion state type corresponding to the physiological features;
   wherein when extracting the physiological features from the physiological feature data, the processor is specifically used for:
   extracting a corresponding age, gender, blood pressure, heart rate, body temperature, and blood oxygen saturation based on the physiological index data;
   extracting a corresponding peak systolic velocity (PSV), end diastolic velocity (EDV), mean flow velocity, resistance index (RI), pulsatility index (PI), and systolic/diastolic ratio based on the cervical blood flow data;
   extracting corresponding cerebral perfusion kinetic parameters based on the ASL data, the QSM data and the qBOLD data, wherein a cerebral blood flow (CBF) is calculated using the ASL data, and the cerebral oxygen metabolism parameters is calculated using the QSM data and the qBOLD data; and
   taking the various physiological features extracted by the physiological index data, the cervical blood flow data, the ASL data and the QSM data as input features of the random forest model;
   wherein when inputting the physiological features into a random forest model to cause a plurality of decision-making trees in the random forest model to predict a cerebral perfusion state type corresponding to the physiological features, the processor is specifically used for:
   inputting the physiological features into the random forest model;
   acquiring feature importance of various physiological features to the random forest model under a preset cerebral perfusion state type;
   sorting the correlations between the various physiological features and the preset cerebral perfusion state type based on the feature importance; and
   screening out, according to a sorting result, the physiological features that are the most correlated to the preset cerebral perfusion state type as the feature subset of the random forest model;
   respectively obtaining, based on the feature subset, a plurality of cerebral perfusion state types to be selected through the plurality of decision-making trees;
   making a vote based on the plurality of cerebral perfusion state types to be selected through the plurality of decision-making trees to obtain a plurality of voting results; and
   taking the cerebral perfusion state type to be selected with the most votes from among the plurality of voting results as a final output prediction result of the random forest model.

2. The apparatus according to claim 1, wherein the physiological feature data comprises physiological feature data samples collected in different types of cerebral perfusion states;

the processor is further used for: the labeling cerebral perfusion state type corresponding to each of the physiological feature data samples.

3. The apparatus according to claim 1, wherein the method for acquiring the feature importance comprises at least one of the Gini index method, the frequency statistics method and the average accuracy reduction method.

4. The apparatus according to claim 1, wherein when acquiring feature importance of various physiological features to the random forest model under a preset cerebral perfusion state type, the processor is specifically used for:
for each of the physiological feature data sample collected in the preset cerebral perfusion state type, calculating a Gini index of the physiological feature in each physiological feature data sample for each decision-making tree in the random forest model, so as to obtain a Gini index of each of the physiological feature for the various decision-making trees in the random forest model.

5. A cerebral perfusion state classification method, comprising:
receiving physiological feature data from different data collection devices, wherein the physiological feature data comprises at least one of physiological index data, cervical blood flow data, and cerebral perfusion data; wherein the cerebral perfusion data comprises cerebral magnetic resonance data, and the cerebral magnetic resonance data comprises arterial spin labeling (ASL) data, quantitative susceptibility mapping (QSM) data, and quantitative Blood Oxygen Level Dependent (qBOLD) data;
extracting physiological features from the physiological feature data, wherein comprises: extracting a corresponding age, gender, blood pressure, heart rate, body temperature, and blood oxygen saturation based on the physiological index data;
extracting a corresponding peak systolic velocity (PSV), end diastolic velocity (EDV), mean flow velocity, resistance index (RI), pulsatility index (PI), and systolic/diastolic ratio based on the cervical blood flow data;
extracting corresponding cerebral perfusion kinetic parameters based on the ASL data, the QSM data and the qBOLD data, wherein a cerebral blood flow (CBF) is calculated using the ASL data, and the cerebral oxygen metabolism parameters is calculated using the QSM data and the qBOLD data; and
taking the various physiological features extracted by the physiological index data, the cervical blood flow data, the ASL data and the QSM data as input features of the random forest model;
inputting the physiological features into a random forest model to cause a plurality of decision-making trees in the random forest model to predict a cerebral perfusion state type corresponding to the physiological features, wherein comprises:
inputting the physiological features into the random forest model;
acquiring feature importance of various physiological features to the random forest model under a preset cerebral perfusion state type;
sorting the correlations between the various physiological features and the preset cerebral perfusion state type based on the feature importance; and
screening out, according to a sorting result, the physiological features that are the most correlated to the preset cerebral perfusion state type as the feature subset of the random forest model;
respectively obtaining, based on the feature subset, a plurality of cerebral perfusion state types to be selected through the plurality of decision-making trees;
making a vote based on the plurality of cerebral perfusion state types to be selected through the plurality of decision-making trees to obtain a plurality of voting results; and
taking the cerebral perfusion state type to be selected with the most votes from among the plurality of voting results as a final output prediction result of the random forest model; and
classifying a cerebral perfusion state based on the cerebral perfusion state type corresponding to the physiological features.

6. A cerebral perfusion state classification model training apparatus, comprising:
a transceiver module used for receiving physiological feature data samples from different data collection devices, wherein the physiological feature data samples comprise at least one of a physiological index data sample, a cervical blood flow data sample, and a cerebral perfusion data sample; wherein the cerebral perfusion data comprises cerebral magnetic resonance data, and the cerebral magnetic resonance data comprises arterial spin labeling (ASL) data, quantitative susceptibility mapping (QSM) data, and quantitative Blood Oxygen Level Dependent (qBOLD) data;
a processor used for extracting physiological feature samples from the physiological feature data samples; inputting the physiological feature samples into a random forest model to cause a plurality of decision-making trees in the random forest model to predict a cerebral perfusion state type corresponding to the physiological feature samples;
wherein when extracting the physiological features from the physiological feature data, the processor is specifically used for:
extracting a corresponding age, gender, blood pressure, heart rate, body temperature, and blood oxygen saturation based on the physiological index data;
extracting a corresponding peak systolic velocity (PSV), end diastolic velocity (EDV), mean flow velocity, resistance index (RI), pulsatility index (PI), and systolic/diastolic ratio based on the cervical blood flow data;
extracting corresponding cerebral perfusion kinetic parameters based on the ASL data, the QSM data and the qBOLD data, wherein a cerebral blood flow (CBF) is calculated using the ASL data, and the cerebral oxygen metabolism parameters is calculated using the QSM data and the qBOLD data; and
taking the various physiological features extracted by the physiological index data, the cervical blood flow data, the ASL data and the QSM data as input features of the random forest model;
wherein when inputting the physiological features into a random forest model to cause a plurality of decision-making trees in the random forest model to predict a cerebral perfusion state type corresponding to the physiological features, the processor is specifically used for:
inputting the physiological features into the random forest model;
acquiring feature importance of various physiological features to the random forest model under a preset cerebral perfusion state type;

sorting the correlations between the various physiological features and the preset cerebral perfusion state type based on the feature importance; and screening out, according to a sorting result, the physiological features that are the most correlated to the preset cerebral perfusion state type as the feature subset of the random forest model;

respectively obtaining, based on the feature subset, a plurality of cerebral perfusion state types to be selected through the plurality of decision-making trees;

making a vote based on the plurality of cerebral perfusion state types to be selected through the plurality of decision-making trees to obtain a plurality of voting results; and taking the cerebral perfusion state type to be selected with the most votes from among the plurality of voting results as a final output prediction result of the random forest model;

and wherein the processor is further used for adjusting, based on a cerebral perfusion state type predicted by the random forest model and a pre-labeled mapping relation between the physiological feature data samples and cerebral perfusion state type samples, the random forest model, so as to cause a cerebral perfusion state type output by the adjusted random forest model to be consistent with the cerebral perfusion state type sample.

7. A cerebral perfusion state classification model training method, comprising:

receiving physiological feature data samples from different data collection devices, wherein the physiological feature data samples comprise at least one of a physiological index data sample, a cervical blood flow data sample, and a cerebral perfusion data sample; wherein the cerebral perfusion data comprises cerebral magnetic resonance data, and the cerebral magnetic resonance data comprises arterial spin labeling (ASL) data, quantitative susceptibility mapping (QSM) data, and quantitative Blood Oxygen Level Dependent (qBOLD) data;

extracting physiological feature samples from the physiological feature data samples, wherein comprises: extracting a corresponding age, gender, blood pressure, heart rate, body temperature, and blood oxygen saturation based on the physiological index data;

extracting a corresponding peak systolic velocity (PSV), end diastolic velocity (EDV), mean flow velocity, resistance index (RI), pulsatility index (PI), and systolic/diastolic ratio based on the cervical blood flow data;

extracting corresponding cerebral perfusion kinetic parameters based on the ASL data, the QSM data and the qBOLD data, wherein a cerebral blood flow (CBF) is calculated using the ASL data, and the cerebral oxygen metabolism parameters is calculated using the QSM data and the qBOLD data; and taking the various physiological features extracted by the physiological index data, the cervical blood flow data, the ASL data and the QSM data as input features of the random forest model;

inputting the selected physiological feature samples into a random forest model to cause a plurality of decision-making trees in the random forest model to predict a cerebral perfusion state type corresponding to the physiological feature samples, wherein comprises:

inputting the physiological features into the random forest model;

acquiring feature importance of various physiological features to the random forest model under a preset cerebral perfusion state type;

sorting the correlations between the various physiological features and the preset cerebral perfusion state type based on the feature importance; and screening out, according to a sorting result, the physiological features that are the most correlated to the preset cerebral perfusion state type as the feature subset of the random forest model;

respectively obtaining, based on the feature subset, a plurality of cerebral perfusion state types to be selected through the plurality of decision-making trees;

making a vote based on the plurality of cerebral perfusion state types to be selected through the plurality of decision-making trees to obtain a plurality of voting results; and taking the cerebral perfusion state type to be selected with the most votes from among the plurality of voting results as a final output prediction result of the random forest model; and adjusting, based on a cerebral perfusion state type predicted by the random forest model and a pre-labeled mapping relation between the physiological feature data samples and cerebral perfusion state type samples, the random forest model, so as to cause a cerebral perfusion state type output by the adjusted random forest model to be consistent with the cerebral perfusion state type sample.

8. An electronic device, comprising a memory and a processor; wherein, the memory is used for storing a program;

the processor is coupled to the memory and used for executing the program stored in the memory to achieve:

receiving physiological feature data from different data collection devices, wherein the physiological feature data comprises at least one of physiological index data, cervical blood flow data, and cerebral perfusion data; wherein the cerebral perfusion data comprises cerebral magnetic resonance data, and the cerebral magnetic resonance data comprises arterial spin labeling (ASL) data, quantitative susceptibility mapping (QSM) data, and quantitative Blood Oxygen Level Dependent (qBOLD) data;

extracting physiological features from the physiological feature data, wherein comprises: extracting a corresponding age, gender, blood pressure, heart rate, body temperature, and blood oxygen saturation based on the physiological index data;

extracting a corresponding peak systolic velocity (PSV), end diastolic velocity (EDV), mean flow velocity, resistance index (RI), pulsatility index (PI), and systolic/diastolic ratio based on the cervical blood flow data;

extracting corresponding cerebral perfusion kinetic parameters based on the ASL data, the QSM data and the qBOLD data, wherein a cerebral blood flow (CBF) is calculated using the ASL data, and the cerebral oxygen metabolism parameters is calculated using the QSM data and the qBOLD data; and taking the various physiological features extracted by the physiological index data, the cervical blood flow data, the ASL data and the QSM data as input features of the random forest model;

inputting the physiological features into a random forest model to cause a plurality of decision-making trees in the random forest model to predict a cerebral perfusion state type corresponding to the physiological features, wherein comprises:

inputting the physiological features into the random forest model;

acquiring feature importance of various physiological features to the random forest model under a preset cerebral perfusion state type;

sorting the correlations between the various physiological features and the preset cerebral perfusion state type based on the feature importance; and screening out, according to a sorting result, the physiological features that are the most correlated to the preset cerebral perfusion state type as the feature subset of the random forest model;

respectively obtaining, based on the feature subset, a plurality of cerebral perfusion state types to be selected through the plurality of decision-making trees;

making a vote based on the plurality of cerebral perfusion state types to be selected through the plurality of decision-making trees to obtain a plurality of voting results; and taking the cerebral perfusion state type to be selected with the most votes from among the plurality of voting results as a final output prediction result of the random forest model; and classifying a cerebral perfusion state based on the cerebral perfusion state type corresponding to the physiological features.

* * * * *